United States Patent
Meier et al.

(10) Patent No.: US 7,011,963 B1
(45) Date of Patent: Mar. 14, 2006

(54) PROCESS FOR SYNTHESIS OF BEAD-SHAPED CROSS-LINKED HYDROPHILIC SUPPORT POLYMER

(75) Inventors: Christian Meier, Darmstadt (DE); Thomas Suefke, Erzhausen (DE); Hans-Ulrich Petereit, Darmstadt (DE); Roger Recktenwald, Bensheim (DE); Thomas Boller, Darmstadt (DE)

(73) Assignee: Roehm GmbH & Co KG, Darmstadt (DE)

( * ) Notice: Subject to any disclaimer, the term of this patent is extended or adjusted under 35 U.S.C. 154(b) by 0 days.

(21) Appl. No.: 09/600,180

(22) PCT Filed: Feb. 1, 1999

(86) PCT No.: PCT/EP99/00635

§ 371 (c)(1),
(2), (4) Date: Dec. 21, 2001

(87) PCT Pub. No.: WO99/40122

PCT Pub. Date: Aug. 12, 1999

(30) Foreign Application Priority Data

Feb. 5, 1998 (DE) .......................................... 198 04 518

(51) Int. Cl.
| | |
|---|---|
| *C12N 11/08* | (2006.01) |
| *C12P 1/00* | (2006.01) |
| *G01N 33/545* | (2006.01) |
| *C07K 17/08* | (2006.01) |
| *A61K 9/14* | (2006.01) |

(52) U.S. Cl. .......................... 435/180; 424/484; 435/41; 435/280; 435/803; 435/815; 436/531; 530/402; 530/412; 530/413; 530/415; 530/815

(58) Field of Classification Search ................. 435/177, 435/180, 181, 41, 815, 803, 280; 424/484; 436/531; 530/402, 412, 415, 815, 413
See application file for complete search history.

(56) References Cited

U.S. PATENT DOCUMENTS

| | | | | |
|---|---|---|---|---|
| 4,070,348 A | * | 1/1978 | Draemer et al. ............ 260/79.3 |
| 4,247,643 A | * | 1/1981 | Kramer et al. .............. 435/178 |
| 4,511,694 A | | 4/1985 | Krämer et al. | |
| 5,294,491 A | | 3/1994 | Goeldner et al. | |
| 5,326,698 A | * | 7/1994 | Kasche et al. .............. 435/231 |
| 5,342,646 A | * | 8/1994 | Kleese et al. ................ 427/2.1 |

* cited by examiner

*Primary Examiner*—David M. Naff
(74) *Attorney, Agent, or Firm*—Oblon, Spivak, McClelland, Maier & Neustadt, P.C.

(57) ABSTRACT

The invention relates to a process for synthesis, by inverse bead polymerization of a monomer phase, of a bead-like, cross-linked, hydrophilic copolymer which has binding activity toward ligands containing nucleophilic groups. The invention relates to support polymer materials with high binding capacity for penicillin acylase and low swelling factor, as well as to use of the same.

20 Claims, No Drawings

PROCESS FOR SYNTHESIS OF BEAD-SHAPED CROSS-LINKED HYDROPHILIC SUPPORT POLYMER

The invention relates to a process for synthesis, by inverse suspension polymerization of a monomer phase, of a bead-like, cross-linked, hydrophilic copolymer which has binding activity toward ligands containing nucleophilic groups. The invention also relates to support polymer materials with high binding capacity for penicillin amidase and low swelling factor, as well as to use of the same.

PRIOR ART

Porous polymer support materials for proteins, especially enzymes, are sufficiently known. Applications exist in medicine, for example, in the enzyme-induced cleavage of β-lactam antibiotics such as penicillin G to 6-aminopenicillanic acid (6-APA) by means of penicillin acylase (penicillin amidase). Important development goals are primarily the highest possible loading capacity, low swelling ability and the lowest possible residual solvent contents. Halogenated solvents should in principle be avoided for synthesis.

German Laid-open Application DE-OS 2237316 describes a process for synthesis of bead-like, cross-linked copolymers by radical polymerization of a monomer mixture containing a radical-forming initiator and comprising a monomer having binding activity toward biological substances, a cross-linking monomer and at least one further comonomer, the said monomer mixture being suspended as droplets and polymerized in a nonpolar organic liquid. Aliphatic hydrocarbons in particular, and above all such with 8 and more C atoms, are suitable as the nonpolar organic liquid.

Mixtures of n-heptane and perchloroethylene are used in the examples. The ratio of the monomer phase to the organic dispersion medium can range between 1:1 and 1:10, but ratios of between 1:1.5 and 1:4 are preferred. German Patent DE A 3106456 describes a process improved compared with DE-OS 2237316 in relation to the binding capacity of the polymer beads. Particularly high binding capacities for proteins, especially for the penicillin acylase (penicillin amidase) enzyme are obtained when the support polymers contain high contents of cross-linking monomers and when the monomer phase, formed from the monomers and the diluent, contains a solvent mixture as diluent. Suitable mixtures can be, for example, water/methanol or formamide/methanol. Monomers and diluents are present in a ratio of about 1:2.6. A mixture of n-hexane and perchloroethylene is used as the organic, dispersion medium. In the examples, the ratio of the monomer phase to the organic dispersion medium is about 1:2.8. When the proportion of cross-linking agent in the monomer mixture is 50 wt % and water/methanol is used as the diluent, there can be obtained support polymers with a binding capacity of up to 125 U/g, measured as penicillin acylase activity.

Object and Achievement

The object of the invention is to provide an improved process for synthesis of bead-like, cross-linked copolymers. It is also the intent to avoid the use of halogenated solvents in the organic dispersion medium and at the same time to achieve a binding capacity of at least 220 [U/g moist] for the penicillin amidase enzyme (EC 3.5.1.11) under standardized conditions (loading of 1 g of support polymer material with 1530 units of penicillin amidase). Furthermore, the swellability of the polymer beads in water should not exceed 1.5, expressed as a swelling factor (ml moist/ml dry).

The object was achieved by a process for synthesis, by inverse bead polymerization of a monomer phase, of a bead-like, cross-linked, hydrophilic copolymer which has binding activity toward ligands containing nucleophilic groups, which monomer phase comprises monomers and a diluent, which contains as monomers
  a) 5 to 40 wt % of hydrophilic monomers which contain a vinyl group, can undergo radical polymerization and form at least 10% aqueous solutions at room temperature
  b) 30 to 50 wt % of monomers which contain a vinyl group and an additional functional group, can undergo radical polymerization and, in a polymer-like reaction with the nucleophilic groups of the ligands, can form covalent bonds
  c) 20 to 60 wt % of hydrophilic, cross-linking monomers which contain two or more ethylene-type unsaturated polymerizable groups and can undergo radical polymerization, with the proviso that a), b) and c) add up to 100 wt %, which uses as diluent a mixture of methanol and water in the ratio of 1:1.0 to 1:4.0, the monomer phase being dispersed as droplets in a dispersion medium comprising an organic solvent chosen from the aliphatic hydrocarbons with 5 to 7 carbon atoms, the ratio of monomer phase to dispersion medium ranging from 1:2.0 to 1:4.0, and which in this form is subjected to radical polymerization in the presence of a polymerization initiator and a protective colloid, with the proviso that the ratio of monomers to diluent ranges from 1:1.7 to 1:2.4.

By application of the inventive process it is possible to obtain a novel support polymer material, which has a loading capacity for penicillin amidase of at least 220 [U/g moist], resulting from the reaction of 1530 units of penicillin acylase with 1 g of support polymer material, and which exhibits a swelling factor of at most 1.5.

It was not foreseeable that the definition of the various process parameters relative to each other would lead to a clearly greater binding capacity for the penicillin amidase enzyme and that at the same time, however, the swellability would decrease. It was also surprising that, by application of the inventive process, the use of halogenated hydrocarbons such as perchloroethylene, which heretofore have been the most widely used compounds for equalizing the densities of the phases, can be avoided by choosing as the organic solvent an aliphatic hydrocarbon with 5 to 7 carbon atoms.

Operation of the Invention

Monomers

In order to ensure that the monomer mixture is hydrophilic, it must comprise predominantly hydrophilic monomers. As hydrophilic monomers there are to be understood such monomers that form at least 10% aqueous solutions at room temperature and preferably do not contain any ionic groups or groups that can be ionized by addition of acids or bases.

Monomers a) comprise 5 to 40 wt %, 8 to 35 wt %, especially 9 to 12 wt % of hydrophilic monomers which contain a vinyl group, can undergo radical polymerization and form at least 10% aqueous solutions at room temperature.

Suitable as monomers a) are in particular acrylamide and/or methacrylamide, but methacrylamide is preferred. Further examples are hydroxyalkyl esters of unsaturated polymerizable carboxylic acids, such as hydroxyethyl acrylate and hydroxyethyl methacrylate or N-vinylpyrrolidone.

Monomers b) comprise 30 to 50 wt %, preferably 35 to 45 wt % of monomers which contain a vinyl group and an additional functional group, preferably an oxirane group (epoxy group), can undergo radical polymerization and, in a reaction analogous to polymerization, can form covalent bonds with the nucleophilic groups of the ligands. Oxirane groups in particular are suitable for binding ligands while preserving their biological activity.

Preferred monomers b) are glycidyl methacrylate and/or allyl glycidyl ether. Especially preferably, both monomers are used in approximately equal proportions at the same time.

Monomers c) comprise 20 to 60 wt %, especially 25 to 55 wt %, especially preferably 40 to 55 wt % of hydrophilic, cross-linking monomers which contain two or more ethylene-type unsaturated polymerizable groups and can undergo radical polymerization. Preferred monomers c) are N,N'-methylenebisacrylamide or N,N'-methylenebismethacrylamide. N,N'-Methylenebismethacrylamide is especially preferred. If necessary, 0 to 10 wt % of further cross-linking monomers which contain two or more ethylene-type unsaturated polymerizable groups and can undergo radical polymerization may also be used. Suitable are hydrophilic di(meth)acrylates such as polyethylene oxide di(meth)acrylates.

Monomers a), b) and c) add up to 100 wt % in all cases.

Diluent

The monomer phase comprises monomers a) to c), which are dissolved in a diluent, which must be a mixture of methanol and water in the ratio 1:1.0 to 1:4.0. Especially favorable mixing ratios for methanol and water range from 1:1.2 to 1:2.5, especially from 1:1.3 to 1:1.7.

Ratio of Monomers to Diluent

The ratio of monomers to diluent is especially critical. It must range from 1:1.7 to 1:2.4, especially preferably from 1.9 to 2.1.

Dispersion Medium

An organic solvent comprising an aliphatic hydrocarbon with 4 to 7 C atoms is suitable as the dispersion medium. n-Heptane is preferred and cyclohexane is especially preferred.

Ratio of Monomer Phase to Dispersion Medium

The ratio of the monomer phase to the dispersion medium formed by the organic solvent must range from 1:2.0 to 1:4.0, preferably from 1:2.8 to 1:3.3.

Further Process Conditions

As further constituents the suspended monomer phase contains polymerization initiators which are known in themselves, preferably sulfur-free initiators and especially preferably 4,4'-azobis-(4-valeric acid), as well as protective colloids (emulsifiers), such as a copolymer comprising 95 parts of n-butyl methacrylate and 5 parts of 2-trimethylammoniumethyl methacrylate chloride with molecular weights (weight-average) in the range of 30,000 to 80,000.

The bead polymerization (also known as suspension polymerization) is otherwise performed in known manner, for example by firstly introducing the dispersion medium and the protective colloid, then dispersing the monomer phase, which also contains the initiator, in the organic phase with stirring at 40 to 60° C., for example, and then heating to 60 to 70° C. The water/methanol mixture can be removed from the loop almost completely in the form of an azeotrope over a period of, for example, 6 hours. The mixture is allowed to react to completion for about 3 to 5 hours and is then cooled to room temperature. The resulting beads are suctioned and dried in vacuum for a period of, for example, 12 hours. Alternatively, the bead polymers can also be filtered off and washed with water. Drying is preferably performed in a fluidized-bed dryer, since in this way solvent residues can be removed particularly effectively. The obtained polymer beads (=support polymer material) have a size in the range of 50 to 500 $\mu$m, especially of 120 to 250 $\mu$m.

By binding capacity there is understood that enzyme activity which can be achieved when the support polymer material is loaded to the maximum with a specified enzyme. An important application of the inventive support polymer material is the cleavage of penicillin G to 6-aminopenicillanic acid (6-APA) by means of bound penicillin amidase from *E. coli*. The binding capacity is expressed as penicillin amidase activity in units per g of support polymer beads [U/g moist]. The binding capacity of the inventive support polymer beads in this measurement method is at least 220 [U/g moist].

The swellability of the polymer beads in water is expressed by the swelling factor [ml moist/ml dry]. The inventive polymer beads exhibit a swelling factor of no greater than 1.5.

Uses of the Inventive Support Polymer Materials

The inventive support polymer materials can be used in stirred or flow reactors for covalent binding of ligands by means of the oxirane groups which they contain. This can be achieved, for example, by addition of proteins, especially enzymes, from concentrated solutions via covalent bonding with retention of their biological activity. Peptides, amino acids, β-lactam antibiotics, lipids, nucleotides, polynucleotides, low molecular weight nucleophilic compounds or metalloorganic compounds can also be reacted with the oxirane groups of the support beads.

The polymer beads loaded with ligands can be used in procedures known in themselves for stereospecific synthesis of chiral substances such as amino acids (d-phenylalanine, p-hydroxy-d-phenylalanine, l-tert-leucine) or of pharmaceuticals such as ibuprofen. They are also used as supports in enzyme-induced cleavage of penicillin G to 6-aminopenicillanic acid (6-APA), of cephalosporin G to 7-aminodesacetoxycephalosporanic acid (7-ADCA) or of cephalosporin C to 7-aminocephalosporanic acid (7-ACA). The process is described in DECHEMA Annual Conference 1996—Abstracts [in German], Vol. 1, DECHEMA e.V. Further applications are specific enzyme-induced syntheses of amoxicillin and ampicillin on substrates such as the above cleavage products. A further application comprises syntheses of fine chemicals or basic products (such as malic acid) for chemical syntheses. The polymer beads can also be used in separation technology for adsorption chromatography or gel permeation chromatography. To achieve specific adsorption, the polymer beads can be loaded with immunoglobulin fractions from antiserums or with monoclonal antibodies. The use of support polymer material loaded with enzymes or antibodies as adsorbent in extracorporeal therapy, in which pathogenic or toxic substance are removed from whole blood, can be cited as yet a further application.

EXAMPLES (The determination method hereinafter is familiar in itself to the person skilled in the art of support polymer materials, and will be described only for the sake of completeness) Determination of the Binding Capacity for Penicillin Amidase (=Penicillin G Acylase) from *E. coli* (EC 3.5.1.11)

a) Covalent Binding of Penicillin Amidase to the Support Polymer Material 1 g of support polymer material was added to 1530 units of penicillin amidase in 5 ml of sterile 1 M potassium phosphate buffer of pH 7.5 and incubated for 48 hours at 23° C.

Thereafter the polymer beads were placed on a sintered glass filter (porosity 2 or 3) and, in a suction process, washed on the filter two times with deionized water and then two times with 0.1 M potassium phosphate buffer of pH 7.5 containing 0.05% ethyl-4-hydroxybenzoate. The moist weight of the resulting beads loaded with penicillin acylase was determined.

b) Determination of the Binding Capacity 250 to 300 mg of moist support polymer material (polymer beads) coupled with penicillin amidase was added to 20 ml of a 2% penicillin G solution in 0.05 M potassium phosphate buffer of pH 7.5, containing 0.05% ethyl4-hydroxybenzoate and maintained at 37° C. Liberated phenylacetic acid was titrated under steady stirring with 0.5 M NaOH at a constant pH of 7.8 for a period of 10 minutes, during which the NaOH consumption was recorded.

Thereafter the polymer beads were collected as under a) on a sintered glass filter by means of suctioning of 20 ml of 0.05 M potassium phosphate buffer of pH 7.5 containing 0.05% ethyl-4-hydroxybenzoate, and the measurement was repeated two times.

c) Calculation of the Binding Capacity

The linear region of the measured curve (usually the region from 1 to 5 minutes) was used as basis for the calculation and extrapolated to an interval of 10 minutes. The binding capacity was expressed as units of penicillin amidase per g of moist support polymer material (U/g moist). One unit corresponds to one $\mu$mol of hydrolyzed penicillin G per minute ($\mu$mol/min); thus 1 liter of 0.5 M NaOH is equivalent to 500 $\mu$mol of hydrolyzed penicillin G. (The water content of the support polymer material is approximately constant and can therefore be disregarded.)

Examples 1 to 3

Test conditions common to Examples 1 to 3:

In a 2-liter stirred flask with thermometer, water separator, reflux condenser and nitrogen admission tube there were placed an organic solvent, 3 g of a copolymer comprising 95 parts of n-butyl methacrylate and 5 parts of 2-trimethylammoniumethyl methacrylate chloride as protective colloid and 5 g of dry ice. Under stirring and passage of nitrogen, there was dispersed in the organic phase at 50° C. a monomer phase comprising water and methanol in a ratio of 1:1.5 as diluent, plus 10 g of methacrylamide,
20 g of allyl glycidyl ether,
20 g of glycidyl methacrylate and
50 g of methylenebismethacrylamide
plus
2 g of 4,4'-azobis-4-cyanovaleric acid (as polymerization initiator), after which the contents were heated to boiling at 65 to 70° C. The mixture was incubated for about 6 hours and then cooled to room temperature. The resulting polymer beads were suctioned, washed and dried in the fluidized-bed dryer. Thereafter the binding capacity for penicillin amidase [U/g moist] and the swelling factor [ml moist/ml dry] were determined.

The main test parameters and the results of Examples 1 to 3 are presented in the following table.

| | Example 1 (according to the invention) | Example 2 (comparison example) | Example 3 (comparison example) |
|---|---|---|---|
| Organic solvent (dispersion medium) | 952 g of cyclohexane | 669 g of cyclohexane | 530 g of n-heptane + 530 g of perchloroethylene |
| Total monomers | 100 g | 100 g | 100 g |
| Diluent | 80 g of methanol + 120 g of water (=1:1.5) | 263 g of formamide | 264 g of formamide |
| Monomers + diluent (monomer phase) | 300 g | 363 g | 364 g |
| Ratio of monomer to diluent | 1:2 | 1:2.63 | 1:2.64 |
| Ratio of monomer phase to dispersion medium | 1:3.2 | 1:1.8 | 1:2.9 |
| Binding capacity for penicillin amidase (1530 U) [U/g moist] | 252 | 194 | 192 |
| Swelling factor [ml moist/ml dry] | 1.3 | 4.0 | 3.9 |

What is claimed is:

1. A process for the synthesis of a bead-shaped, cross-linked, hydrophilic copolymer, comprising:
    radically polymerizing a monomer phase, in a bead polymerization process, in the presence of a polymerization initiator and a protective colloid,
    the monomer phase comprising:
        monomers, and
        a diluent,
    the monomer phase being present during the polymerization in dispersed form as droplets in a dispersion medium comprising an organic solvent selected from the group consisting of aliphatic hydrocarbons with 5 to 7 carbon atoms;
    to thereby obtain said bead-shaped, cross-linked, hydrophilic copolymer, the copolymer having a binding activity toward ligands containing nucleophilic groups,
    wherein said monomer phase comprises as monomers
    a) 5 to 40 wt % of hydrophilic monomers which contain a vinyl group, said hydrophilic monomers being capable of radical polymerization, and being capable of forming at least 10% aqueous solutions at room temperature,
    b) 30 to 50 wt % of monomers which contain a vinyl group and an additional functional group, said monomers being capable of radical polymerization and being capable of forming at least one covalent bond in a reaction with at least one nucleophilic group of a ligand, and
    c) 20 to 60 wt % of cross-linking monomers which contain two or more ethylenically unsaturated polymerizable groups, said cross-linking monomers being capable of radical polymerization,
    wherein a), b) and c) add up to 100 wt %, wherein said monomer phase comprises as diluent a mixture of methanol and water in the ratio of 1:1.0 to 1:4.0, wherein a ratio of monomer phase to dispersion medium ranges from 1:2.0 to 1:4.0, and wherein a ratio of monomers to diluent ranges from 1:1.7 to 1:2.4.

2. The process according to claim 1, wherein said monomers are
   a) acrylamide, methacrylamide or mixtures thereof,
   b) glycidyl methacrylate, allyl glycidyl ether or mixtures thereof,
   c) methylenebisacrylamide or methylenebismethacrylamide.

3. The process according to claim 1, wherein said organic solvent is cyclohexane.

4. The process according to claim 1, wherein said monomer a) is a methacrylamide.

5. The process according to claim 1, wherein said functional group of monomer b) is an oxirane group.

6. The process according to claim 1, wherein said ligand of said nucleophilic group is an oxirane group.

7. The process according to claim 1, wherein said monomer c) is N, N'-methylenebismethacrylamide.

8. The process according to claim 1, wherein said ratio of monomers to diluent is from 1:1.9 to 1:2.1.

9. The process according to claim 1, wherein said ratio of monomer phase to dispersion medium is from 1:2.8 to 1:3.3.

10. The process according to claim 1, wherein said protective colloid is a copolymer comprising 95 parts of n-butyl methacrylate and 5 parts of 2-trimethylammoniumethyl methacrylate chloride having a weight average molecular weight of from 30,000 to 80,000.

11. The process according to claim 1, wherein said copolymer has a size of from 50 to 500 µm.

12. A support polymer material obtained by the process according to claim 1, said support polymer having a binding capacity for penicillin amidase from *E. coli* of at least 220 U/g moist, based on a reaction of 1530 units of penicillin amidase with 1 g of said support polymer material, and said support polymer having a swelling factor of at most 1.5.

13. A method of binding proteins, comprising:
    contacting the support polymer material according to claim 12, with at least one protein.

14. A method of binding enzymes, comprising:
    contacting the support polymer material according to claim 12 with at least one enzyme.

15. A method of binding antibodies, comprising:
    contacting the support polymer material according to claim 12 with at least one antibody.

16. A method of chromatography, comprising:
    contacting the support polymer material according to claim 12 with at least one compound.

17. A method for synthesis of pharmaceuticals, comprising:
    synthezising a pharmaceutical in the presence of the support polymer material according to claim 12.

18. A method for stereospecific synthesis of chiral substances, comprising:
    synthezising a chiral substance in the presence of the support polymer material according to claim 12.

19. A method of covalently binding of a ligand, comprising:
    contacting the support polymer material according to claim 12 with a ligand to covalently bind the ligand to the support polymer material;
    wherein said support polymer material has an oxirane group.

20. A support polymer material loaded with a ligand and obtained by the method according to claim 19.

* * * * *

UNITED STATES PATENT AND TRADEMARK OFFICE
CERTIFICATE OF CORRECTION

| | | |
|---|---|---|
| PATENT NO. | : 7,011,963 B1 | Page 1 of 1 |
| APPLICATION NO. | : 09/600180 | |
| DATED | : March 14, 2006 | |
| INVENTOR(S) | : Meier et al. | |

It is certified that error appears in the above-identified patent and that said Letters Patent is hereby corrected as shown below:

On the title page, Item 86, the Filing Date is incorrect. Item 86 should read:

-- (86) PCT No: PCT/EP99/00635

§ 371 ©(1),
(2), (4) Date: Dec. 21, 2000

Signed and Sealed this

Twenty-second Day of August, 2006

JON W. DUDAS
*Director of the United States Patent and Trademark Office*